United States Patent [19]

Kronenthal et al.

[11] Patent Number: 4,568,536

[45] Date of Patent: Feb. 4, 1986

[54] CONTROLLED RELEASE OF PHARMACOLOGICALLY ACTIVE AGENTS FROM AN ABSORBABLE BIOLOGICALLY COMPATIBLE PUTTY-LIKE COMPOSITION

[75] Inventors: Richard L. Kronenthal, Fair Lawn; Frank V. Mattei, Piscataway; Alan J. Levy, Bridgewater, all of N.J.

[73] Assignee: Ethicon, Inc., Somerville, N.J.

[21] Appl. No.: 687,692

[22] Filed: Feb. 8, 1985

[51] Int. Cl.$^4$ .................. A61K 9/02; A61K 9/06; A61K 9/20; A61K 47/00
[52] U.S. Cl. ........................... 424/22; 424/19; 514/772; 514/777; 514/784; 514/785; 514/900; 514/902; 514/953; 514/960; 514/964; 514/965; 514/969
[58] Field of Search ............... 424/19, 22; 514/772, 514/777, 784, 785, 900, 902, 953, 960, 964, 965, 969

[56] References Cited

U.S. PATENT DOCUMENTS

| | | | |
|---|---|---|---|
| 3,312,594 | 4/1967 | Cyr et al. | 424/19 |
| 3,429,308 | 2/1969 | Russell | 128/1 |
| 3,444,858 | 5/1969 | Russell | 129/260 |
| 3,978,203 | 8/1976 | Wise | 424/22 |
| 4,059,686 | 11/1977 | Tanaka et al. | 424/19 |
| 4,130,639 | 12/1978 | Shalaby et al. | 424/78 |
| 4,186,189 | 1/1980 | Shalaby et al. | 424/78 |
| 4,250,163 | 2/1981 | Nagai et al. | 424/81 |
| 4,292,299 | 9/1981 | Suzuki et al. | 424/16 |
| 4,439,420 | 3/1984 | Mattei et al. | 424/78 |
| 4,440,789 | 4/1984 | Mattei et al. | 424/78 |
| 4,443,430 | 4/1984 | Mattei et al. | 424/78 |

*Primary Examiner*—Shep K. Rose
*Attorney, Agent, or Firm*—Leonard Kean

[57] ABSTRACT

An absorbable biologically compatible putty-like composition is used as a matrix from which immunologically or pharmacologically active agents, such as antibiotics, can be introduced into the body to provide a slow sustained release of the agent over an extended period of time. A preferred matrix comprises a mixture of calcium stearate, dextran and castor oil.

4 Claims, 3 Drawing Figures

FIG-2 Mc IN ABSORBABLE BONE WAX RELEASE KINETICS

CONTROLLED RELEASE OF PHARMACOLOGICALLY ACTIVE AGENTS FROM AN ABSORBABLE BIOLOGICALLY COMPATIBLE PUTTY-LIKE COMPOSITION

This invention relates to an absorbable biologically compatible putty-like composition which is used as a matrix from which immunologically or pharmacologically active agents, such as antibiotics, can be introduced into the body to provide a slow, sustained release of the agent over an extended period of time. A preferred matrix comprises a mixture of calcium stearate, dextran and castor oil.

BACKGROUND OF THE INVENTION

Drugs are conventionally administered orally or via injection, often at a site remote from the target. Over a relatively short period of time, the drug diffuses into the circulation system of the patient and is distributed to the various organs and tissues, at least one of which is the intended target for the drug. The action of the drug on organs other than the target may result in undesirable side effects. Finally, the drug is metabolized or otherwise irreversibly removed from the organism by excretion or chemical deactivation. When drugs are delivered orally or by injection, the level and duration of availability of the drug cannot be controlled independently; only the size and frequency of the dose can be manipulated. Typically, there is an initially high concentration of available drug at the site of injection or in the circulatory system which then decreases gradually as the drug is distributed and consumed within the body of the patient.

In controlled, sustained delivery, a formulation of drug and a carrier is administered to the patient by injection or implantation. The carrier forms a drug reservoir that protects the stored drug from extraneous removal mechanisms and releases the drug to the biological reservoir at a predetermined rate. Controlled, sustained delivery of a drug prevents undesirable peaking of blood levels and makes the drug available at an optimum and uniform concentration over an extended period of time. Only the released drug is subject to removal via metabolism and excretion. In the controlled, sustained delivery method, there is potential for control of the drug release rate by factors inherent in the delivery package itself. Some of these inherent factors, such as the rate of hydrolysis of an absorbable polymer, or the rate of transdermal diffusion, are in contrast to the externalized controls associated with classical delivery methods, e.g., rate of tablet intake, frequency of injections, etc. In accordance with prior methods, the maintenance of therapeutic blood levels of an antibiotic, for example, requires a fairly precise dosing of tablets. Though this may be uncomplicated for many adults, it may be difficult where gastric problems are present or for infants, the very infirm, or in veterinary work, such as with range animals.

The present invention provides a device that may be implanted on a one-time basis and which releases and maintains reasonably effective and predictable drug levels, thus eliminating the need for continual external supervision. Known methods for controlled release of drugs include the anthelmintic bolus based on an absorbable polymer. Another method which has been commercialized is the transdermal delivery of life-maintaining drugs such as nitroglycerine.

The present invention relates to the system wherein a controlled-release drug system/package is placed in or close to the target area. A great advantage of this system is that the medication does not have to traverse needless miles of the vascular system, become diluted and inactivated in countless organs and tissues, all of which may lead to undesirable side effects, and all of which is usually compensated for by overdosing, thus even further accentuating undesirable side effects.

The present invention provides a localized device/system which delivers effective doses of a drug, such as an antibiotic, directly to the affected target area, in which the matrix or releasing medium is completely absorbable. An example thereof are the gums in cases of periodontal diseases.

The present device may be dispensed in the shape of a pellet. In addition, several medications may be combined in one pellet, for example, an antibacterial (or an antibiotic combined with a non-antibiotic medication), combined with an anti-inflammatory agent, a corticosteroid and a pain killer such as benzocaine, thus preventing complete therapy to the infected area.

The compositions of the present invention possess a putty-like consistency at room and body temperatures and thus may be easily and conveniently shaped by hand, into the form most desirable for placement in a pocket in the body from which sustained release of a medicament is desirable (such as the naturally formed pocket between the base of a tooth and the adjoining tissues, when the composition is used in connection with periodontal disease). In addition to this moldability by hand, these compositions also additionally conform to body or tissue or organ contours by yielding to gentle pressures in the implant area without becoming runny, or losing their consistency. Prior art sustained release compositions do not possess a putty-like consistency at room and body temperatures and thus lack the above-described advantages of the composition of the present invention.

A very unique characteristic of this type of consistency and rheology lies in its response to elevated temperatures. Thus, while some compositions (either pure compounds, or polymers or waxes, for example) remain solids up to the melting/softening temperature, and soften or melt above this temperature, the present matrix shows only a barely perceptible softening upon heating. Thus, for example, while the polyalkene oxalates of Shalaby, et al. in U.S. Pat. No. 4,186,189, are either rigid solids (non-conformable, irritating as implants) below the melting point, or runny liquids above the melting temperature (and thus will flow away from the target area into unwanted tissues and organs) the present matrix will maintain its moldable, conformable consistency over a very wide range of temperatures.

A preferred composition of the present invention includes a matrix consisting of calcium stearate, dextran and castor oil. The consistency of this composition may be easily altered merely by increasing the castor oil content and, indeed, this adjustment allows the composition to be pushed through a standard dental syringe with little effort. As has been shown experimentally, the consistency can also be varied without altering the ratio of components. If the matrix is prepared as a composition, the consistency of which is adequate for bone hemostasis, it can be made considerably more rigid by passing it through a 3-roll mill. The resulting material which has not been altered chemically, may now be ideal for packing around infected gums by means of a spatula. The calcium stearate, dextran and castor oil compositions containing varying concentrations of meclocycline sulfosalicylate were evaluated in vitro for release rate characteristics. Release rates of the antibiotic in buffer were monitored at several temperatures and were found to be extremely regular, predictable and at therapeutic levels. These compositions, containing the meclocycline sulfosalicylate, thus possess excellent release rates, easily adjustable consistency and, in addition, the absorption rates of the entire composites may be controlled via adjustment of the dextran content. This composition can furthermore be prepared without need for degradative and stressful conditions (such as temperature, time, catalysts, etc.). All of these features provide an excellent medium or matrix for controlled drug release. In contrast, the prior art sustained-release compositions do not possess the above-described advantages.

Certain of the compositions of the present invention also constitute absorbable bone waxes so that when an antibiotic is incorporated therein, the compositions, when used in the conventional manner as bone waxes, are provided with antimicrobial activity. This helps prevent infection of the bone marrow which is of concern in the field of orthopedics where shattered limbs may be infected before the surgeon operates.

The present composition is also advantageous in the field of immunology. During the normal injection of an antigen (killed viruses, synthetic polypeptides, etc.) dispersed in saline solution, for example, the contents of the injection may course through the entire body within the span of an hour or two. This leads to a "flash" effect, a peak reaction (fever, rashes, etc.) and is generally of short duration which requires periodic booster shots. If the same antigen were to be incorporated in the matrix of the present invention and extruded as a filament under the skin (using a dental syringe, for example) the antigen would be released at a rate that is controlable in the same manner as the other applications described herein. This predictable, controllable, uniform rate, would release levels of antigen conducive to the most effective build-up of antibody, and in its sustained action would avoid peak/flash side effects as well as the need for booster shots.

In accordance with the present invention, the pharmacologically active agent may be an anti-cancer drug such as a chemotherapeutic agent or a radioactive isotope such as iodine 125. The composition incorporating an anti-cancer agent could be extruded as a rod right into the affected sites or pellets could be implanted in or near the affected area. Shapes of special design or consistency may also be implanted.

In accordance with one embodiment of the present invention, the pharmacologically active agent may consist of magnetic particles which are blended into the absorbable putty-like composition which is then implanted in the body and used in connection with hyperthermia therapy.

In accordance with a further embodiment of the present invention, when used as an anti-cancer composition, natural iodine is incorporated into the absorbable putty-like matrix and stored as such. Thereafter, just prior to use, the iodine is converted to a radioactive isotope by exposure in an atomic pile. With respect to such use, it must be ensured that other radioactive species, which may be generated, are not too long-lived or toxic.

THE PRIOR ART

The Shalaby et al. U.S. Pat. No. 4,186,189 discloses that absorbable polymers derived from alkylene oxalates may be formulated with a drug and introduced into the body to provide a slow, sustained release of the drug over an extended period of time in accordance with the rate of absorption of the polymer. The composition of Shalaby et al. does not have a putty-like consistency at room temperature (nor does it accomodate itself to fit snugly and smoothly in the contours of surrounding tissues) and would, thus, not be suitable for manipulating pellets into different desired shapes for implantation into the body, nor would such composition be suitable to act as a medicated bone-wax.

The Mattei et al. U.S. Pat. Nos. 4,439,420; 4,443,430 and 4,440,789 disclose various absorbable hemostatic compositions for use in the control of osseous hemorrhage, said compositions each possessing a comformable putty-like consistency at room temperature. No pharmacologically active agents are disclosed in any of said patents.

U.S. Pat. Nos. 4,130,639 and 3,978,203 describe compositions which are formulated with a drug and which may be introduced into the body to provide a slow, sustained release of the drug over an extended period of time. However, such compositions do not possess a putty-like consistency at room temperature and, thus, pellets thereof could not suitably be molded by hand into different shapes prior to insertion in a body pocket (nor do they have the faculty for accomodating themselves to the surrounding contours), nor would such compositions be suitable for use as anti-microbial bone-waxes.

SUMMARY OF THE INVENTION

The present invention relates to a pharmaceutical depot composition for administration of at least one pharmacologically or immunologically active agent released slowly over an extended period of time, which comprises a combination of (a) from 0.25% to 50% by weight of the composition of a pharmacologically active agent in an effective depot amount greater than the single dose amount and (b) a matrix which is non-reactive towards body tissue and which is absorbable in the body over an extended period of time without adverse body reaction; the matrix being an absorbable composition having a putty-like consistency at room and body temperatures. The matrix is also completely free of fibrous materials.

The preferred matrix utilized in accordance with the present invention is the absorbable composition disclosed in the Mattei et al. U.S. Pat. No. 4,439,420. This patent is incorporated herein by reference.

Said preferred matrix consists of an absorbable composition comprising: (i) a component (A) comprising either a biocompatible, fatty acid salt alone, which comprises between 45% and 80% by weight based on the weight of the matrix, or a mixture of said fatty acid salt with a biocompatible in vivo absorption enhancing agent, in which said mixture comprises between 35% and 60% by weight of said fatty acid salt based on the weight of the matrix, and between 10% and 35% by weight of said absorption enhancing agent based on the weight of the matrix, and the remainder of the matrix consisting of (i) a component (B) comprising a body absorbable, biocompatible base consisting of a natural or synthetic oil or wax which is absorbable in the body, the cation of the fatty acid salt being selected from the group consisting of calcium, magnesium, zinc and aluminum; the fatty acid anion being saturated or unsaturated and containing from 10 to 22 carbon atoms in the chain, said composition having a putty-like consistency at room and body temperatures. Component (B) preferably comprises a body absorbable, biocompatible base selected from the group consisting of ethylene oxide/propylene oxide block copolymers, polyethylene glycols and methoxypolyethylene glycols, triglycerides and fatty acid esters. The absorption enhancing agent is preferably selected from the group consisting of Carbowax, Pluronics, glycerine, propylene glycol, sodium, potassium or ammonium stearates, palmitates, etc. but most preferably dextran.

When the absorption enhancing agent is dextran, the rate of absorption of the matrix in the body can be controlled by varying the dextran content.

In accordance with one embodiment of the composition of the present invention, the matrix consists of an absorbable composition comprising: (i) a component (A) comprising a mixture of a biocompatible, fatty acid salt with a biocompatible in vivo absorption enhancing agent, in which said mixture comprises between 35% and 45% by weight of said fatty acid salt, based on the weight of the matrix and between 25% and 35% by weight of said absorption enhancing agent based on the weight of the matrix; (ii) at least 20% by weight of a component (B) comprising a body absorbable, biocompatible base selected from the group consisting of ethylene oxide/propylene oxide block copolymers, polyethylene glycols and methoxypolyethylene glycols, triglycerides and fatty acid esters, and up to 10% by weight of water, the cation of said fatty acid salt being selected from the group consisting of calcium, magnesium, zinc and aluminum; the fatty acid anion being saturated or unsaturated and containing from 10 to 22 carbon atoms in the chain, the composition having a putty-like consistency at room and body temperatures.

In accordance with a preferred embodiment of the present invention, the matrix consists of an absorbable composition comprising (i) a component (A) comprising a mixture of calcium stearate and dextran in which said mixture comprises between about 35% and about 60% by weight of said calcium stearate based on the weight of the matrix and between about 10% and about 35% by weight of dextran based on the weight of the matrix; the remainder of the matrix comprising (ii) a component (B) comprising a biocompatible base consisting of a natural or synthetic oil or wax which is absorbable in the body, said composition having a putty-like consistency at room and body temperatures. The preferred component (B) is castor oil.

In one preferred composition of the invention, the matrix comprises about 41% by weight of calcium stearate, about 30% by weight of dextran and about 29% by weight of castor oil.

Component (B) used in said matrix is preferably selected from the group consisting of sesame oil, sweet almond oil, castor oil, cottonseed oil, olive oil, cod liver oil, peanut-oil, safflower oil, soya oil and corn oil.

A further embodiment of the present invention comprises a composition in which the matrix consists of a synthetic, absorbable composition comprising from 60% to 80% by weight of said matrix of purified polydioxanone in a biocompatible base, said polydioxanone having an inherent viscosity in hexafluoroisopropanol at a concentration of 0.1 g/dl and at a temperature of 25° C. of between about 0.03 and 0.15, said base comprising a natural or synthetic oil or wax which is absorbable in the body, said polydioxanone having a sufficiently low inherent viscosity such that the mixture with the base is workable and softenable by hand to bring about a putty-like consistency at room and body temperatures. The base is preferably selected from the group consisting of isopropyl palmitate, sesame oil, castor oil, almond oil, ethylene oxide/propylene oxide block copolymers, polyethylene glycols and methoxypolyethylene glycols. A preferred matrix is one in which the polydioxanone comprises between 65% and 75% (and most preferably about 68%) by weight of the matrix. The preferred base is sesame oil and the preferred inherent viscosity of the polydioxanone is about 0.1.

The polydioxanone in a biocompatible base is fully described in U.S. Pat. No. 4,440,789 which is incorporated herein by reference.

Yet a further embodiment of the present invention is one in which the matrix consists of a synthetic absorbable material comprising a copolymer of lactide and glycolide containing from about 30% to 70% lactide on a molar basis, having a molecular weight such that it is workable and softenable by hand to bring about a putty-like consistency at room and body temperatures, said copolymer having an inherent viscosity in hexafluoroisopropanol at a concentration of 0.1 g/dl and at a temperature of 25° C. of between about 0.03 and 0.1. A lactide/glycolide copolymer containing from 60% to 70% lactide on a molar basis is preferred and most preferred is a material in which the lactide/ glycolide ratio is about 65/35 on a molar basis. The above synthetic absorbable material may optionally include a biocompatible base which is non-chemically reacting and which is capable of forming a solution or gel with said material. Said biocompatible base is preferably selected from the group consisting of calcium stearate, glyceryl monostearate and water.

Said copolymer of lactide and glycolide preferably possesses a molecular weight of between about 2,000 and 2,500 and preferably the copolymer has an inherent viscosity in hexafluoroisopropanol at a concentration of 0.1 g/dl and at a temperature of 25° C. of between about 0.03 and 0.1 (most preferably about 0.05).

Said lactide/glycolide copolymer is fully described in U.S. Pat. No. 4,443,430 which is incorporated herein by reference.

The pharmacologically active agent which is incorporated into the composition of the present invention may be any drug in the very broad sense as defined in the Federal Food, Drug and Cosmetic Act Section 201(2)g. Thus, the agent may include any article intended for use in the cure, medication, treatment or prevention (immunological applications) of disease in man or animals; or articles (other than food) intended to affect the structure or any function of the body of man or animals. Among the pharmacologically active agents which may be incorporated into the composition of the present invention are anti-microbial agents (including antibiotics), anti-cancer agents, anti-psychotic agents, anti-anxiety agents, anti-depressants, stimulants, analgesics, anorexigenic agents, magnetic particles used for hyperthermia treatments, bone growth factors, pharmacodynamic agents, antigens for immunological work, chemotherapeutic agents, agents affecting metabolic diseases, hormones, steroid and non-steroidal anti-inflammatory agents, vitamins, anti-epilepsy agents, endocrine agents, fertility control agents and anti-helmintics.

In addition, the matrix can be used to release therapeutic levels of dietary supplments such as metals, trace elements, etc. to combat certain conditions including anemia etc.

In the instance wherein said pharmacologically active agent is an anti-microbial agent, said agent is preferably present to the extent of about 0.25% to 10% (and more preferably between 1% and 6%) by weight of the composition of the present invention. A preferred composition of the present invention comprises calcium stearate ranging between 38% and 42%, dextran ranging between 28% and 31%, castor oil ranging between 27% and 30% and a pharmacologically active agent, preferably meclocycline sulfosalicylate, ranging between 1% and 6% by weight of the composition. Two or more pharmacologically active agents may be present in the composition of the present invention. Thus, the composition may include an anti-bacterial agent combined with an anti-inflammatory agent and a pain killer.

BRIEF DESCRIPTION OF THE DRAWINGS

The invention will appear more clearly from the following detailed description when taken in connection with the following drawings.

In the drawings.

DESCRIPTION OF THE INVENTION

Figure 1:
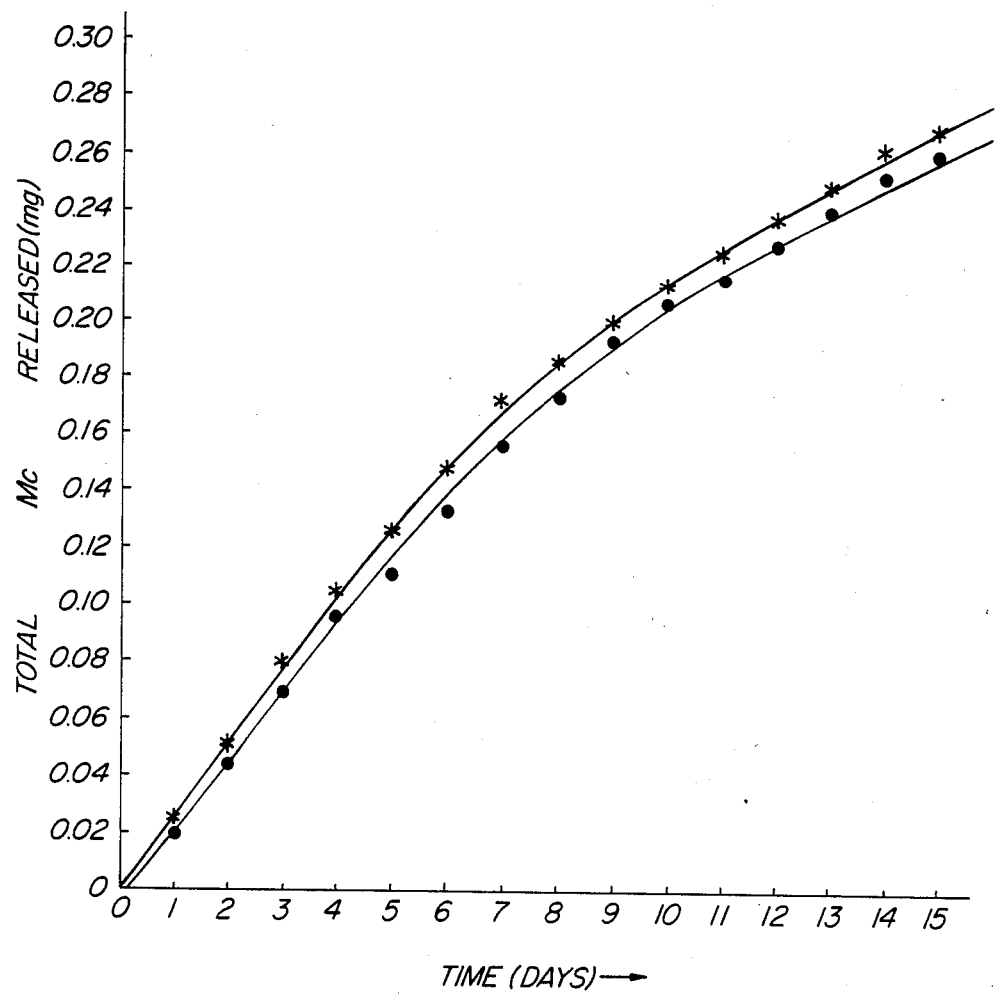
FIGS. 1, 2 and 3 are graphs illustrating the release kinetics of meclocycline in one preferred composition of the present invention. The graphs illustrate the in vitro release of meclocycline from the composition of the present invention, as a function of time.

In accordance with the present invention, an absorbable, putty-like composition is used as a matrix from which pharmacologically active agents, such as antibiotics, can be introduced into the body to provide a slow, sustained release of the agent over an extended period of time. A preferred matrix comprises a mixture of calcium stearate, dextran and castor oil.

In accordance with one embodiment of the present invention, effective doses of antibiotic may be delivered directly to the affected target area, namely the gums in cases of periodontal diseases, in which the matrix or releasing medium is completely absorbable. The composition of the invention is dispensed in the shape of a pellet or a disc or a tiny gumdrop initially, and the final form is determined by accommodativeness of the matrix material to the contours of the target area. The present device might be a pre-measured pellet weighing between 25 to 100 mg., depending on jaw and tooth size and can be provided as a pencil-lead type rod in which the desired length is cut off with a scissors. In one preferred composition, the antibiotic is meclocycline sulfosalicylate, although several classes of antibiotics may be used. Alternatively, the anti-bacterial could also be derived from a non-antibotic. The mode of placement of the controlled, released drug pellet is to tease the gum away from the tooth just enough so that the pellet can be inserted into and lie in a naturally formed pocket between the base of the tooth and the adjoining tissues, thus trapping itself in place. The fluids that normally bathe this area extract out the medications and induce absorption of the pellet which further releases additional medication.

The present invention also relates to the process of releasing a controlled, effective amount of a parenteral depot pharmacologically active agent in an animal or human being over an extended period of time, the improvement comprising administering the composition of the invention to an animal or human.

The following example is provided to further illustrate an embodiment of the present invention.

EXAMPLE

The following four compositions were prepared by mixing together the individual constituents as follows, the percentages being weight percentages of the total compositions:

|  | A | B | C | D (Control) |
|---|---|---|---|---|
| Calcium Stearate EA, PC Grade | 40.39% | 39.77% | 38.95% | 41.0% |
| Dextran "5", Spray Dried | 29.55% | 29.10% | 28.50% | 30.0% |
| Castor Oil | 28.57% | 28.13% | 27.55% | 29.0% |
| Meclocycline Sulfosalicylate | 1.50% | 3.0% | 5.0% | — |
| Totals | 100.0% | 100.0% | 100.0% | 100.0% |

The above simple mixing is advantageous over the known method of chemically reacting a pharmacologically active agent with a polymer chain. No heat is required to admix (avoiding possible drug degradation and/or formation of new species). Rate of drug release is not tied into chain scission and absorption of polymer and oligomers. Consistency and hydrophile/lypophile balance are easily adjusted by slight changes in the proportions of the dextran or the castor oil, or mastication procedures.

The consistency and handling properties of all of the above compositions were judged to be excellent.

With respect to compositions A, B and C, although the meclocycline sulfosalicylate was initially admixed together with the other ingredients, the compositions could just as well have been prepared by masticating the antibiotic with the already prepared control composition D.

The above compositions were first prepared as "chewing gum sticks". However, they could easily be remolded by gentle pressure alone to any desired form.

The above compositions A, B and C are all suitable for maintaining a therapeutic concentration of antibiotic for sufficient time to eliminate infectious organisms in the gingival pocket, in the case of periodontal disease. These compositions have the following properties: they are biodegradable, non-toxic, non-immunogenic, non-carcinogenic, they possess adequate release rates over a 38 day period and they can be adapted for retention in the gingival pocket.

Release Kinetics of Meclocycline Sulfosalicylate (Mc) From Absorbable Bone Wax Studies were carried out on the release kinetics of Mc from composition D above containing 1.1% Mc, 2.6% Mc and 5.2% Mc respectively. For the purpose of the following description, composition D will be referred to as absorbable bone wax (ABW). In each case, a 0.5 g. sample of ABW/Mc (meclocycline sulfosalicylate) was placed into 100 mls of 0.1M phosphate buffer, pH 7.4, and the system was kept at either 23° C. or 38° C. The extraction buffer was changed frequently in order to ensure that sink conditions were maintained and that the rate controlling step was the release of drug from the ABW matrix. Samples were withdrawn from the extraction buffer periodically, and the meclocycline concentration of the buffer was determined spectrophotometrically.

As a result of these studies, it was determined that at room temperature, the amount or percent of drug released from the bone wax matrix is directly proportional to the time the bone wax remained in contact with the extraction buffers. When plotted as a percent of total drug loads, the release rates for the 1.1% and 2.6% Mc samples were nearly identical (at both 23° C. and 38° C.); the 5.2% Mc sample released at a somewhat slower percent rate.

Thereafter, studies were conducted of the in vitro release kinetics of meclocycline sulfosalicylate (Mc) from ABW using human serum as the extraction medium. For a period of 15 days, a drug/absorbable bone wax sample was transferred daily to a freshly prepared 1:1 mixture of reconstituted human serum (NHS; originally lyophilized) and phosphate buffer saline (PBS). After each 24 hour period, the spent extraction medium was spectrophotometrically analyzed for the amount of meclocycline released from the bone wax matrix.

This experiment was designed to more closely simulate the absorption conditions encountered in the actual in vivo situation (with the attendant enzymatic action of body fluids) thereby leading to a more realistic set of release rate kinetics.

Figure 2:
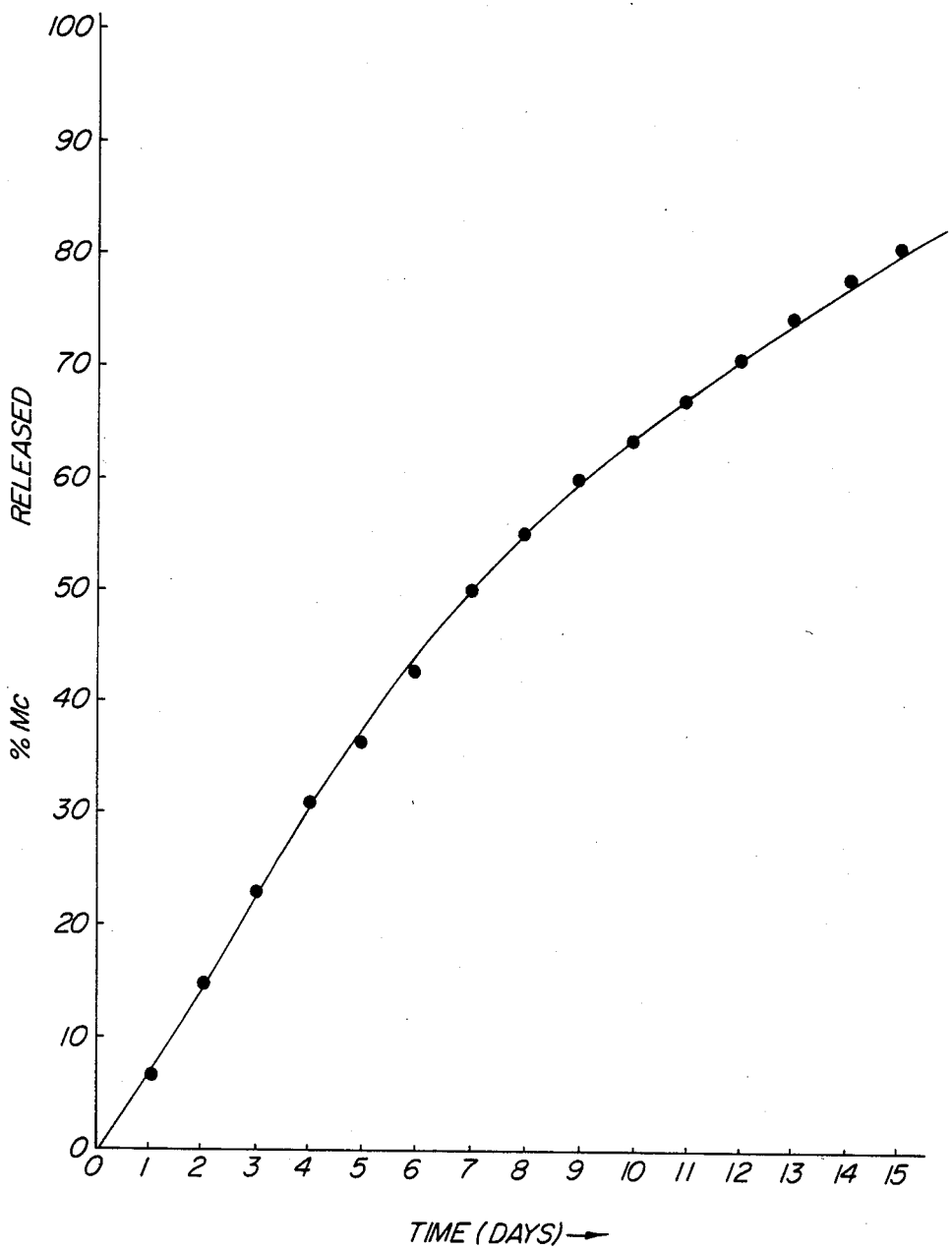
Figure 3:
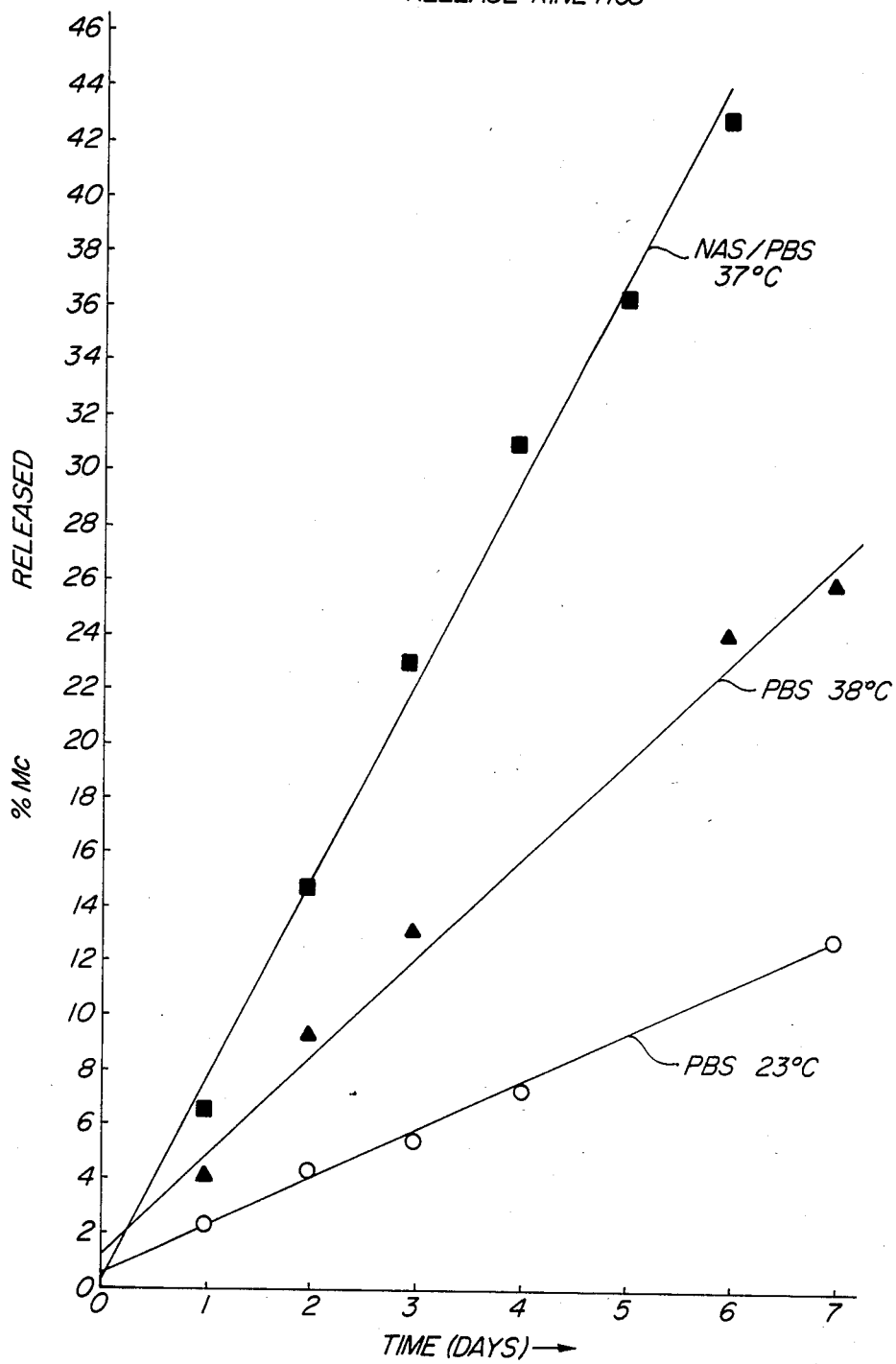

The results are shown in FIGS. 1, 2 and 3 (all of which relate to tests conducted with absorbable bone wax containing 1.1% meclocycline sulfosalicylate).

FIG. 1 displays the duplicate run raw data plots of the amount of meclocycline sulfosalicylate released as a function of time into the diluted serum. It will be noted that the rate of drug delivery follows zero-order release kinetics, at least through the first nine days or approximately 60% of the drug load (i.e., the amount of drug released from the bone wax matrix is directly proportional to the time the bone wax remained in contact with the extraction medium). In FIG. 2, the average of 2 runs (expressed as percent of drug released) is plotted against time. Finally, in FIG. 3, the release rate from the 1.1% Mc/ABW systems is compared for phosphate buffer at 23° C., phosphate buffer at 38° C., and human serum/phosphate buffered saline (PBS) at 37° C. It can be clearly seen from FIG. 3 that the presence of serum enzymes in the extraction medium approximately doubled the rate of drug release over that measured in the simple phosphate buffer. As a rough estimate, the absorbable bone wax samples lost approximately 40% of their weight during the 15 day test period.

Summarizing the above discussion, it will be seen that the release rates of the meclocycline sulfosalicylate antibiotic in buffer (both with and without added enzymes) were found to be extremely regular, predictable and are believed to be at excellent therapeutic levels.

In order to ensure that the meclocycline sulfosalicylate, which was released from the bone wax into serum during the 24 hour incubation period, was still biologically active, a microbiological activity assay was developed, which tested the ability of the drug present in the serum extraction fluid to inhibit growth of two selected strains of orally isolated microorganisms. It was found that the drug maintained its full anti-microbial activity through processing into the absorbable bone wax and after release into human serum.

Having now described the invention in detail, it should be readily apparent to one skilled in the art that there are various modifications and alterations which may be made without departing from the spirit and scope of the present invention.

What is claimed is:

1. In a peridontal desease gum treating method for administration of at least one pharmacologically or immunologically active agent released slowly over an extended period of time to infected or target area pockets between the base of a tooth and the adjoining periodontal tissues, which comprises a combination of
    (a) from 0.25% to 50% by weight of the composition of a pharacologically or immunologically active agent in an effective depot amount greater than the single dose amount, and (b) a matrix which is minimally reactive towards body tissue and which is absorbable in the body over an extended period of time without adverse body reaction; the improvement comprising employing as said matrix dispensed in the shape of a rod, pellet, disc or tiny gum drop, to a pocket formed by teasing the gum away from the tooth an absorbable composition comprising:
        (i) a component (A) comprising a mixture of calcium stearate and dextran in which said mixture comprises between about 35% and about 60% by weight of said calcium stearate based on the weight of the matrix and between about 10% and about 35% by weight of dextran, based on the weight of the matrix; and the remainder of the matrix comprising
        (ii) a component (B) comprising a biocompatible base consisting of a natural or synthetic oil or wax which is absorbable in the body,
said composition having a putty-like consistency at room and body temperatures.

2. The method of claim 1 in which component (B) is selected from the group consisting of sesame oil, sweet almond oil, castor oil, cottonseed oil, olive oil, cod liver oil, safflower oil, soya oil, peanut oil and corn oil.

3. In a peridontal disease gum treating method for administration of at least one pharmacologically or immunologically active agent released slowly over an extended period of time to infected or target area pockets between the base of a tooth and the adjoing periodontal tissues, which comprises a combination of
    (a) from 0.25% to 50% by weight of the composition of a pharmacologically or immunologically active agent in an effective depot amount greater than the single dose amount, and
    (b) a matrix which is minimally reactive towards body tissue and which is absorbable in the body over an extended period of time without adverse body reaction; the improvement comprising employing as said matrix dispensed in the shape of a rod, pellet, disc or tiny gum drop, to a pocket formed by teasing the gum away from the tooth an absorbable composition comprising between about 35% and about 45% by weight of calcium stearate, between about 10% and about 35% by weight of dextran, the remainder of said matrix comprising castor oil.

4. The method of claim 3, wherein said matrix comprises about 41 weight percent of calcium stearate, about 30 weight percent dextran and about 29 weight percent castor oil.

* * * * *

UNITED STATES PATENT AND TRADEMARK OFFICE
CERTIFICATE OF CORRECTION

PATENT NO. : 4,568,536

DATED : February 4, 1986

INVENTOR(S) : Kronenthal et al.

It is certified that error appears in the above-identified patent and that said Letters Patent is hereby corrected as shown below:

Claim 1, line 1, delete "desease" and insert -- disease --.

Claim 1, line 14, delete "pharacologically" and insert -- pharmacologically --.

Signed and Sealed this

Nineteenth Day of August 1986

[SEAL]

Attest:

DONALD J. QUIGG

Attesting Officer

Commissioner of Patents and Trademarks